United States Patent [19]

Jungbauer et al.

[11] Patent Number: 5,676,837

[45] Date of Patent: Oct. 14, 1997

[54] METHOD FOR STERILIZING LIQUID CHROMATOGRAPHY RESINS HIGHLY RESISTANT TO OXIDATION AND A STERILIZATION SOLUTION FOR USE THEREIN

[75] Inventors: Alois Jungbauer; Hans Peter Lettner, both of Vienna, Austria

[73] Assignee: BioSepra, Inc., Marlborough, Mass.

[21] Appl. No.: 662,262

[22] Filed: Jun. 7, 1996

Related U.S. Application Data

[63] Continuation of Ser. No. 251,854, May 31, 1994, abandoned.

[51] Int. Cl.$^6$ ................................................ B01D 15/08
[52] U.S. Cl. .................... 210/635; 210/656; 210/759; 210/764; 210/198.2; 422/28; 422/30
[58] Field of Search ........................ 210/635, 656, 210/759, 764, 198.2, 501, 502.1; 422/28, 30

[56] References Cited

U.S. PATENT DOCUMENTS

| | | | |
|---|---|---|---|
| 3,976,636 | 8/1976 | Salmond | 260/239.55 R |
| 4,585,885 | 4/1986 | Bernhard | 556/436 |
| 4,587,264 | 5/1986 | Jourdan-Laforte et al. | 514/557 |
| 4,743,447 | 5/1988 | Le Rouzic et al. | 424/130 |
| 4,986,963 | 1/1991 | Corcoran et al. | 422/30 |
| 5,008,079 | 4/1991 | Wutzler et al. | 422/28 |
| 5,077,008 | 12/1991 | Kralovic et al. | 422/37 |
| 5,268,097 | 12/1993 | Girot et al. | 210/198.2 |
| 5,268,144 | 12/1993 | Heilmann et al. | 422/26 |
| 5,279,735 | 1/1994 | Cosentino et al. | 210/321.69 |

OTHER PUBLICATIONS

Adner et al., "Biotechnology Product Validation, Part 3: Chromatography Cleaning Validation," BioPharm, pp. 44–48 (Apr., 1994).

Flemming, "Microbial Growth on Ion Exchangers," Wat. Res., vol. 21, No. 7, pp. 745–756 (1987).

Leaper, "Synergistic killing of spores of *Bacillus subtilis* by peracetic acid and alcohol," *Journal of Food Technology*, 19:355–360 (1984).

*Primary Examiner*—Ernest G. Therkorn
*Attorney, Agent, or Firm*—Kriegsman & Kriegsman

[57] ABSTRACT

A method for sterilizing liquid chromatography resins that are highly resistant to oxidation by strongly oxidizing agents and a sterilization solution for use therein. In a preferred embodiment, the invention comprises contacting an oxidant-resistant chromatographic resin with an aqueous solution of peracetic acid and up to 40% ethanol. In particular, where the solution is to be used to sterilize a positively charged ion-exchange resin, the solution preferably additionally includes an acetate buffer of a sufficient ionic strength to prevent adsorption of the peracetic acid ions on the resin.

27 Claims, 5 Drawing Sheets

METHOD FOR STERILIZING LIQUID CHROMATOGRAPHY RESINS HIGHLY RESISTANT TO OXIDATION AND A STERILIZATION SOLUTION FOR USE THEREIN

This application is a continuation of application Ser. No. 08/251,854 filed on May 31, 1994, now abandoned.

FIELD OF THE INVENTION

The present invention relates generally to methods for sterilizing liquid chromatography resins and relates more particularly to a new method for sterilizing liquid chromatography resins that are highly resistant to oxidation by strongly oxidizing agents. The present invention also relates to a sterilization solution for use in sterilizing chromatographic resins that are highly resistant to oxidation by strongly oxidizing agents.

BACKGROUND OF THE INVENTION

Liquid chromatography is one of the most powerful and commonly-used techniques available today for the purification of biomolecules from solutions. Examples of applications to which liquid chromatography has been put include the removal of microbial toxins from pharmaceutical preparations, the isolation of recombinant proteins from cell-culture fractions, and the like. As can readily be appreciated, for many such applications, it is highly undesirable for the chromatographic resin to become colonized by and/or contaminated with microbes since such microbes may affect the purity of any preparation which comes into contact with said resin. Accordingly, it is conventional to apply some sort of sterilization technique to chromatographic resins both before use and between successive uses.

Several different techniques for sterilizing chromatographic resins currently exist. Most of these techniques involve treatment of the resin with a sterilizing chemical agent, either before or after the resin is packed in a column. The choice of the particular agent is largely dependent on the specific resin being sterilized.

One example of a commonly-used sterilizing agent is ethanol/water at neutral or, more preferably, acidic pH. Aqueous ethanol displays its best germicidal efficiency at a concentration of 60% to 70%. However, the most commonly used concentration of aqueous ethanol is about 20% because higher concentrations require explosion-proof facilities. Unfortunately, at 20%, ethanol has no sporicidal effect, its effect on viral inactivation is only partial, and it does not destroy pyrogens. Instead, 20% ethanol only tends to destabilize large molecular aggregates of lipopolysaccharide molecules. For these reasons, 20% ethanol can only be considered to be bacteriostatic agent. Mixtures of ethanol with bases or acids are somewhat more sporicidal but are not sporicidal enough to enable sterilization in reasonably short incubation times and at reasonably low temperatures.

Another example of a commonly-used sterilizing agent is sodium hydroxide. Sodium hydroxide is widely used in the biotech industry both to regenerate and to sterilize chromatography resins. The conditions under which sodium hydroxide is used as a sterilization agent can vary considerably in terms of concentration (0.1N to 1N), incubation times (hours to several days), temperature and column volumes passed through the column (from 1 to more than 10). Sodium hydroxide at concentrations of 0.1 to 0.2N for 30 minutes at room temperature can sometimes destroy pyrogens present on a chromatographic column. In this respect, sodium hydroxide is superior to ethanol since pyrogens are practically unaffected by ethanol but are sensitive to alkaline hydroxide. Nevertheless, as can be seen by referring to FIGS. 1(a) and 1(b) of the present drawings, even at concentrations of 0.5N for incubation periods of several hours, sodium hydroxide is not completely effective at inactivating sporulated germs of B. subtilis. (B. subtilis is used herein as the model microbe per recommendations of the Pharmacopoeia and the American Microbial Society. In the various evalutions of sterilization agents discussed in the present application, B. subtilis is stored as a concentrated stock solution in distilled water at 4° C., and appropriate amounts of spores are transferred into the agent of investigation.) In fact, as can be seen, tens of hours are necessary to reduce significantly the germ concentration of B. subtilis spores using NaOH. (One may wish to compare the results depicted in FIGS. 1(a) and 1(b) with those depicted in FIGS. 2(a) and 2(b) wherein the inactivation kinetics of 0.2N NaOH in 40% ethanol are shown to be improved as compared to those of 0.5N NaOH.)

Other chemicals commonly used to sterilize chromatographic columns include acids (e.g., HCl), detergents such as sodium N-lauroyl sarcosinate (SLS), and, where the resins are resistant enough, $CF_3COOH$, $CHCl_3$ and mixtures of $CHCl_3$ and ethanol. Unfortunately, the sporicidal effect of these agents is not very high and certain of these chemicals are hazardous to both men and materials.

In contrast with the aforementioned techniques currently used to sterilize chromatographic resins, many known techniques commonly used to sterilize medical instruments and the like have not been used to sterilize chromatographic resins. For example, the highly effective technique of destroying microbes by dry or wet heat has not been employed as a sterilization technique due to the temperature sensitivity of most resins. Similarly, sterilization by radiation has not been an option due to the hazards of radiation, particularly in the industrial environments in which chromatographic resins are typically used. Gaseous germicidal agents, such as beta propiolactone and ethylenoxide, have not been considered appropriate for chromatographic resin sterilization due to their chemical reactivity and explosiveness. Similarly, formaldehyde solutions have not been considered appropriate for chromatographic resin sterilization due to the alleged carcinogenic (or at least potent allergenic) nature of formaldehyde. Strongly oxidizing agents have also not been used in the past as chromatographic sterilization agents since it has been recognized by those in the art that most chromatographic resins would rapidly become both physically and chemically degraded if exposed to such oxidizing agents.

One type of strongly oxidizing agent that has been used commonly in the past to sterilize medical instruments and the like is sodium hypochlorite. In addition to possessing excellent germicidal properties, sodium hypochlorite is harmless to human skin and mucoses. Unfortunately, however, the utility of sodium hypochlorite as a sterilization agent is limited by the fact that it generates toxic chlorinated by-products.

Another type of strongly oxidizing agent that has been used commonly in the past to sterilize medical instruments and the like are percarboxylic acids, particularly peracetic acid. For example, in U.S. Pat. No. 5,279,735, which is incorporated herein by reference, there is disclosed a solution for use in sterilizing the hollow, fibrous membranes of hospital dialysis units, the solution comprising a percarboxylic acid, such as peracetic acid, and a colorant that is color stable for a useful period in the oxidizing, sanitizing environment.

Similarly, in U.S. Pat. Nos. 4,986,963 and 4,743,447, both of which are incorporated herein by reference, there are disclosed various compositions for disinfecting contact lenses. One such composition includes an aqueous solution of hydrogen peroxide and peracetic acid. The other composition includes about 0.0001% to 10.0% by weight peracetic acid.

Additional patents disclosing the use of peracetic acid or peracetic acid containing solutions as sterilants include U.S. Pat. Nos. 5,268,144, 5,077,008, 5,008,079 and 4,587,264, all of which are incorporated herein by reference. These four patents involve the use of peracetic acid-based sterilants in the sterilization of instruments used in the medical and food industries.

In addition to being an excellent microbicide, peracetic acid overcomes one of the drawbacks associated with the sodium hypochlorite in that it decomposes into harmless endproducts (i.e., water, acetic acid and oxygen). However, to reiterate, despite its use in sterilizing instruments of the type mentioned above, peracetic acid has not been used in the past to sterilize chromatographic resins for the reasons given above.

In U.S. Pat. No. 5,268,097, which is incorporated herein by reference, there is disclosed a novel class of chromatographic resins, the resins being highly resistant to strongly oxidizing agents. The subject resins comprise a porous solid matrix having interior and exterior surfaces and innate (i.e., inherently present) groups that render the matrix susceptible to undesirable non-specific interaction with biological molecules, and a polymer network derived from a passivation mixture comprising effective amounts of a main monomer, a passivating monomer different from the main monomer, and a crosslinking agent, the mixture having been allowed to come into intimate contact with the surfaces of the matrix for a sufficient period of time such that, on polymerization of the mixture, the innate groups of the matrix become deactivated, resulting in the minimization or substantial elimination of the above-mentioned undesirable non-specific interactions.

SUMMARY OF THE INVENTION

It is an object of the present invention to provide a novel method for sterilizing chromatographic resins highly resistant to strongly oxidizing agents.

It is another object of the present invention to provide a method as described above that overcomes at least some of the drawbacks associated with existing methods for sterilizing oxidation-resistant chromatographic resins.

It is yet another object of the present invention to provide a method as described above that possesses high microbicidal efficiency but that does not result in degradation of the chromatographic resin acted upon.

It is still yet another object of the present invention to provide a method as described above that can be used with chromatographic resins arranged in fluidized-beds, packed-beds, or other modes of operation.

It is a further object of the present invention to provide a method as described above that can be used to sterilize oxidation-resistant chromatographic resins either before or after they have been packed in a column and/or that can be used to sterilize packed resins between successive separations.

It is still a further object of the present invention to provide a sterilization solution for use in practicing the above-described method.

In furtherance of these and other objects to be described or to become apparent below, a method for sterilizing a chromatographic resin highly-resistant to oxidation is provided herein, the method comprising the step of contacting the resin with an aqueous solution of a percarboxylic acid. Preferably, the percarboxylic acid is peracetic acid, and more preferably, the aqueous solution further includes up to 40% ethanol. Where the solution is to be used to sterilize a positively charged ion-exchange resin, the solution preferably additionally includes an acetate buffer of a sufficient ionic strength to prevent adsorption of the peracetic acid ions on the resin.

Additional objects, features and advantages of the present invention will be set forth in part in the description which follows, and in part will be obvious from the description or may be learned by practice of the invention. The embodiments of the present invention will be described in sufficient detail to enable those skilled in the art to practice the invention, and it is to be understood that other embodiments may be utilized and that changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the accompanying drawings, which are hereby incorporated into and constitute a part of this specification.

DETAILED DESCRIPTION OF PREFERRED EMBODIMENTS

Figure 1A:
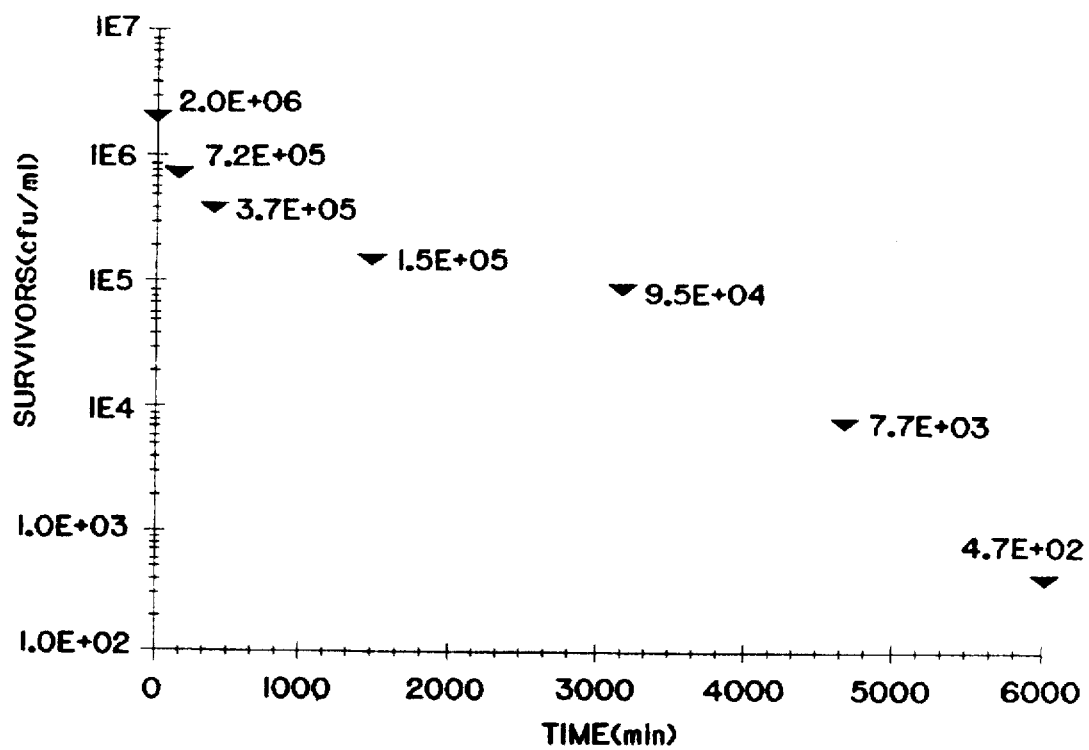
FIGS. 1(a) and 1(b) are graphic representations of the inactivation kinetics of 0.5N NaOH applied against spores of Bacillus subtilis at 4° C. and at 25° C., respectively.
Figure 1B:
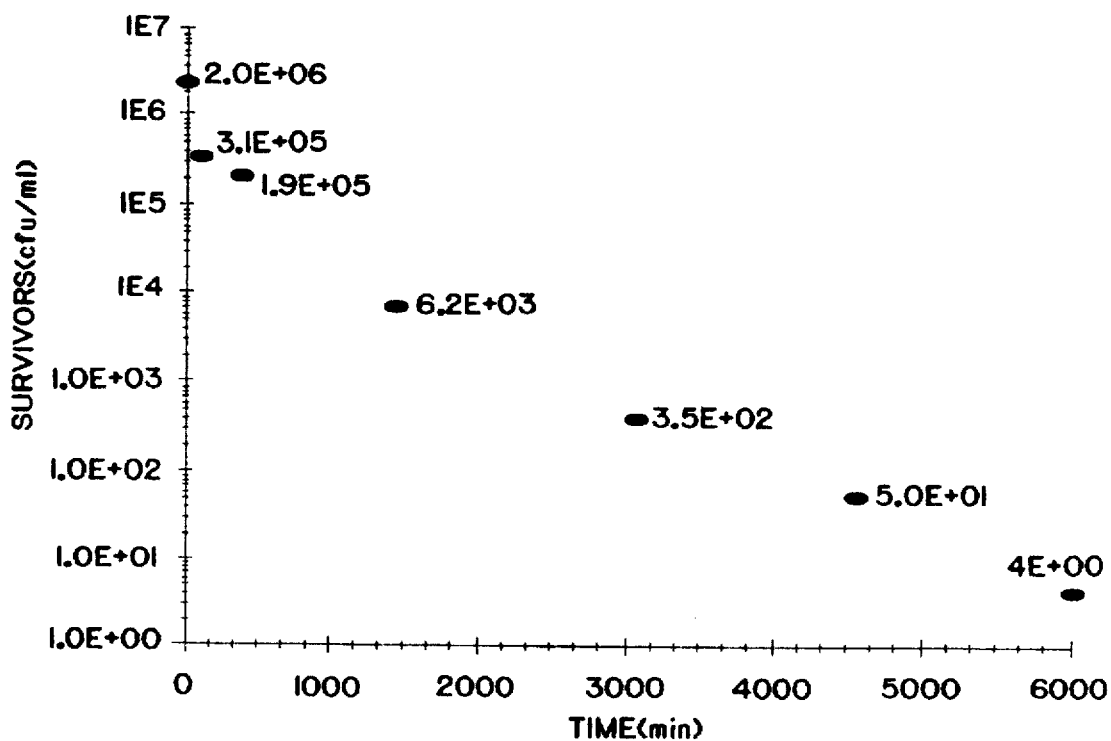
Figure 2A:
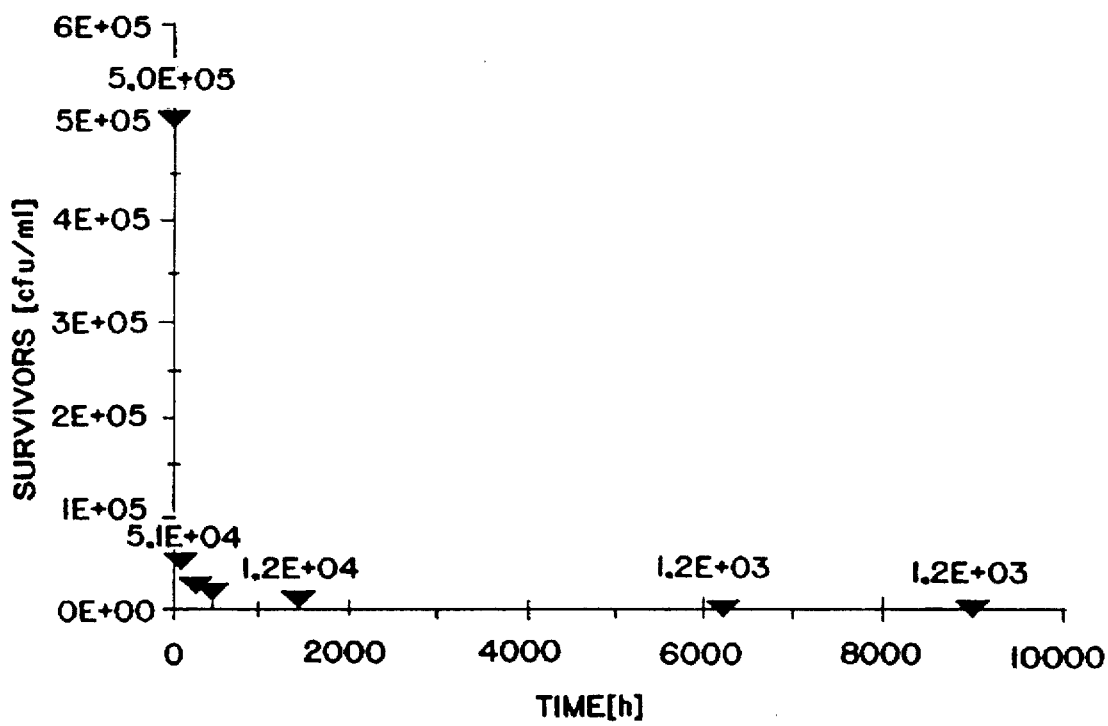
FIGS. 2(a) and 2(b) are graphic representations of the inactivation kinetics of 0.2N NaOH in 40% ethanol applied against spores of Bacillus subtilis at 4° C. and at 25° C., respectively.
Figure 2B:
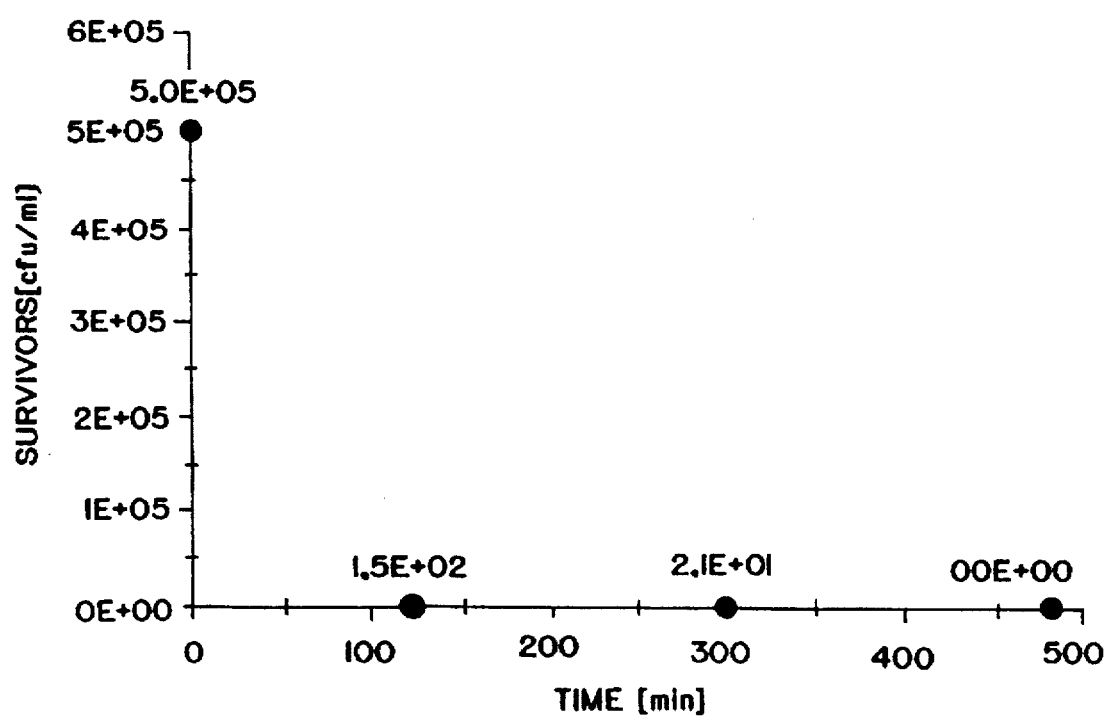

The present invention is directed both to a new method for sterilizing chromatographic resins that are highly resistant to strongly oxidizing agents and to a sterilization solution for use in said method. Examples of oxidation-resistant chromatographic resins are disclosed in U.S. Pat. No. 5,268,097 and are commercially available from BioSepra, Inc. (Marlborough, Mass.) under the family of HyperD™ chromatography sorbents.

The present invention makes use of the unexpected discovery that chromatographic resins that are highly-resistant to oxidation can be sterilized by contacting the resin with an aqueous solution of a percarboxylic acid. Preferably, the percarboxylic acid is peracetic acid, and the concentration of peracetic acid is at least 500 mg/l, more preferably between 1500 mg/l and 5000 mg/l.

The present invention also makes use of the unexpected discovery that improved microbicidal effects, particularly at low temperatures, can be obtained by the addition of an alcohol, preferably ethanol, to the percarboxylic acid-containing solution. The concentration of ethanol may be as high as about 40% but is preferably about 20% due to its flammability.

Where the solution is to be used to sterilize a positively charged ion-exchange resin, the solution preferably further includes a component for raising the ionic strength of the solution to a sufficiently high level to prevent adsorption of the peracetic acid ions on the resin. (Adsorption of the peracetic acid ions on the resin is obviously undesirable because adsorbed peracetic acid ions are unavailable for use in sterilizing the resin, thereby lowering the effective activity of the solution.) Components, such as NaCl, are not suitable for use in raising the ionic strength of the solution because they, themselves, tend to become oxidized by peracetic acid. Applicants have found, however, that acetate buffer, preferably about 0.1 to 2M acetate buffer and more preferably about 0.5M acetate buffer, can withstand the oxidizing power of peracetic acid and is, therefore, a suitable component for raising the ionic strength of the solution.

Preferably, the sterilizing solution of the present invention has a pH of about 5.0. This pH was chosen as an accommodation between the competing interests of (1) the effectiveness of peracetic acid (the lower the pH of peracetic acid, the greater its microbicidal effect) and (2) common chromatographic conditions (pH between about 5.0 and 9.0).

The sterilizing solution of the present invention should not include heavy metals since they accelerate the decomposition of peracetic acid. Also, the storage of the sterilizing solution of the present invention for long periods of time before use is not recommended. Instead, the solution should be prepared immediately before use.

To sterilize an oxidation-resistant chromatographic resin using the sterilization solution of the present invention, one can store the resin, before using it, in the solution; alternatively, one can pack the resin into a chromatographic column and then wash the resin by pouring the solution through the column. The solution can be used to wash packed resins between successive separations and can be used to sterilize resins arranged in fluidized-beds, packed-beds and other modes of operation.

For example, to sterilize a re-equilibrated packed column using the sterilization solution of the present invention, one could use the following procedure: First, the packed column is filled with two system volumes of an inert buffer (0.5M sodium acetate, pH 5.0). Then, after freshly preparing the sterilization solution, one system volume of the sterilization solution is pumped through the column to displace the buffer. Another system volume of the sterilization solution is then recycled through the column for 30 minutes at room temperature, i.e., approximately 20° C. to 25° C. (If the sterilization solution contains 20% ethanol, the contact time should be increased 5-fold for washings performed at 4° C.; if the sterilization solution does not contain ethanol, the contact time should be increased 10 to 20-fold for washings performed at 4° C.) The sterilization solution is then displaced from the column by pumping two system volumes of an inert buffer (0.5M sodium acetate, pH 5.0) through the column.

The information presented below is provided merely to illustrate certain aspects of the present invention and is not intended to limit the present invention in any way. Accordingly, the present invention is best defined by the appended claims.

EXAMPLE I

Preparation of a Sterilizing Solution Containing 1500 mg/l Peracetic Acid in 0.5M Sodium Acetate Buffer, pH 5.0

First, an acetate buffer was prepared by adding 160 millimoles acetic acid (i.e. 9.61 g of 100% acetic acid supplied as 10 g of 96% acetic acid) and 340 millimoles sodium acetate (i.e., 27.9 g of $CH_3COONa$) to approximately 900 ml distilled water. The pH of the resultant buffer solution was 5.08. Next, 19.7 millimoles peracetic acid was added to the buffer. (Peracetic acid is commercially available in 32–40% stock solutions; therefore, 4.69 g of a 32% stock solution would have to be added to the buffer to obtain a concentration of 1500 mg/l.) Finally, distilled water was added to the solution to arrive at a volume of 1 liter. The final pH of the solution was $5.00\pm0.03$.

EXAMPLE II

Preparation of a Sterilizing Solution Containing 1500 mg/l Peracetic Acid and 20% Ethanol in 0.5M Sodium Acetate Buffer, pH 5.0

The procedure recited above in connection with Example 1 was repeated, with the following exception: an appropriate quantity of up to 40% (w/v) ethanol was used instead of distilled water to arrive at a final concentration of 20% ethanol.

EXAMPLE III

Figure 3A:
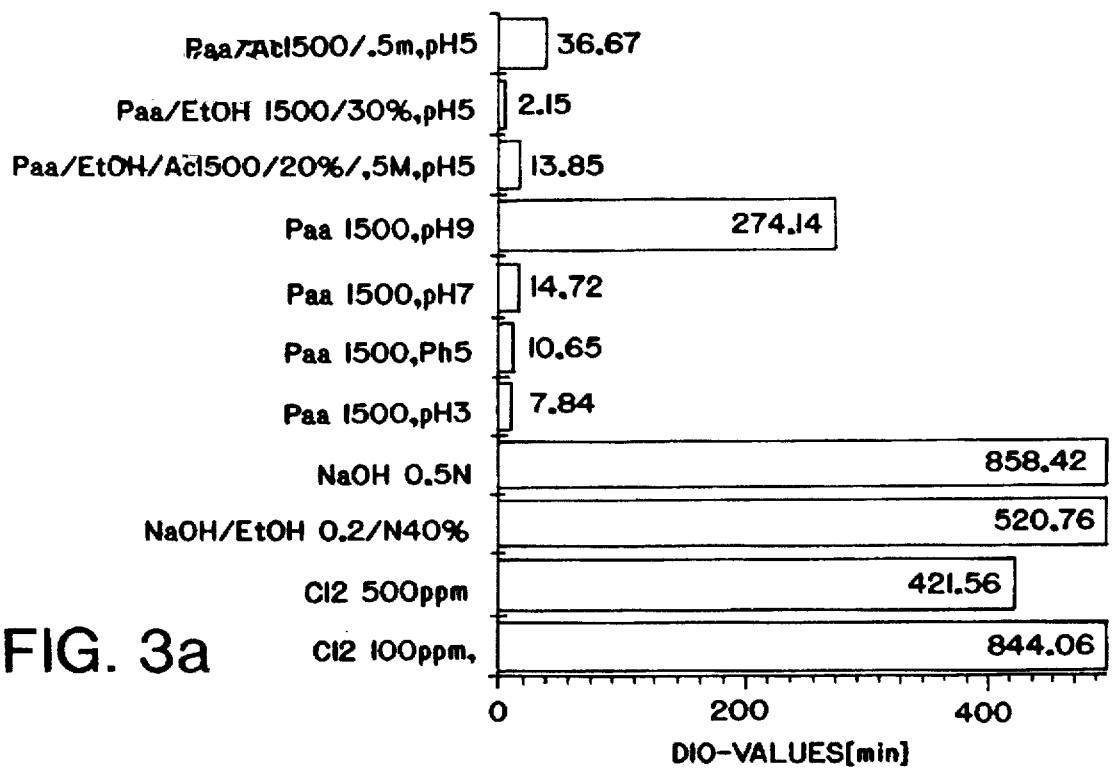
FIGS. 3(a) and 3(b) are graphic representations of the $D_{10}$ values of various sterilization agents applied against spores of Bacillus subtilis at 4° C. and at 25° C., respectively (wherein Paa 1500 represents 1500 ppm peracetic acid; Cl2 100/500 ppm represents hypochlorite 100/500 ppm available chlorine; Ac 0.5M represents 0.5M sodium acetate buffer; and EtOH 20/30% represents 20/30 (v/v) % ethanol)
Figure 3B:
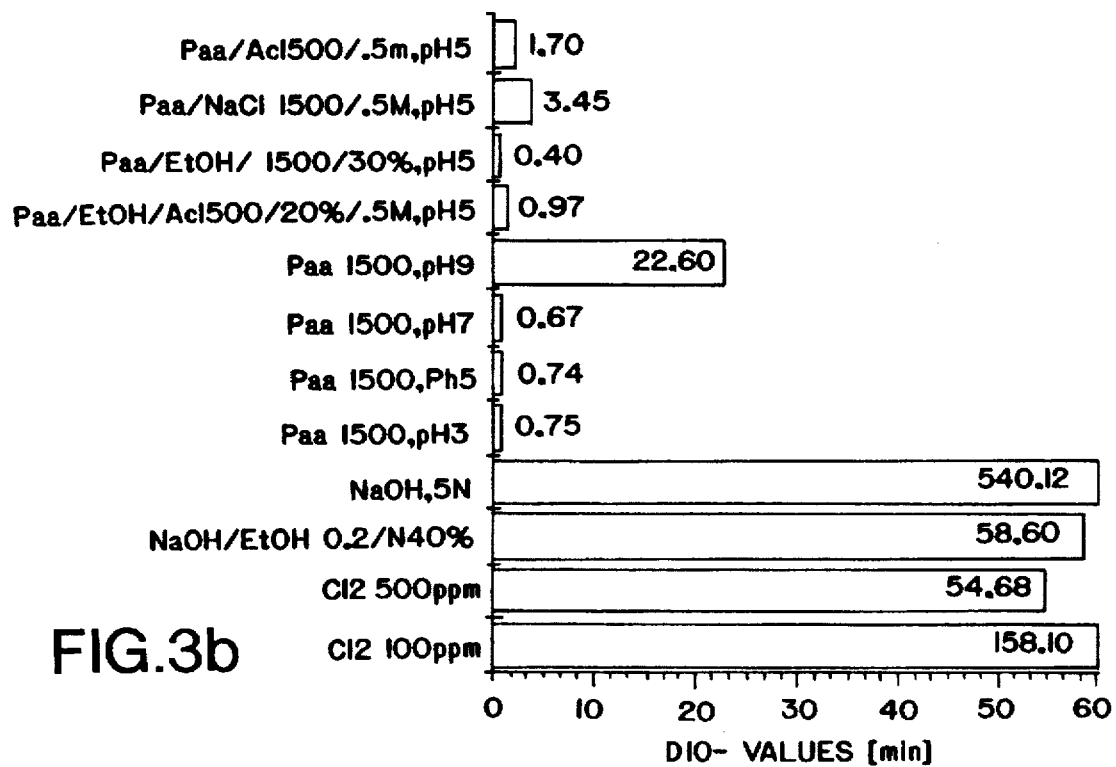
Figure 4A:
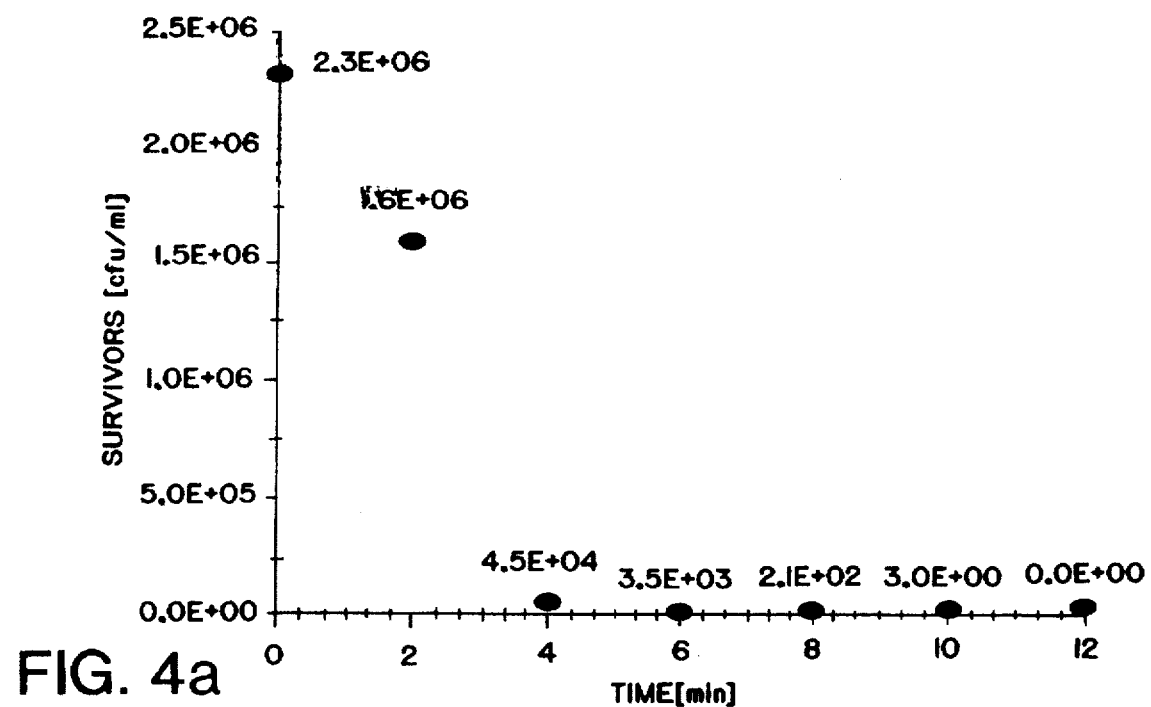
FIGS. 4(a) through 4(d) are graphic representations of the inactivation kinetics of (a) 1500 ppm peracetic acid buffered in 0.5M sodium acetate buffer, pH 5, at 25° C.; (b) 1500 ppm peracetic acid in 20% ethanol buffered in 0.5M sodium acetate buffer, pH 5, at 25° C.; (c) 1500 ppm peracetic acid buffered in 0.5M sodium acetate buffer, pH 5, at 4° C.; and (d) 1500 ppm peracetic acid in 20% ethanol buffered in 0.5M sodium acetate buffer, pH 5, at 4° C., respectively, applied against spores of Bacillus subtilis.
Figure 4B:
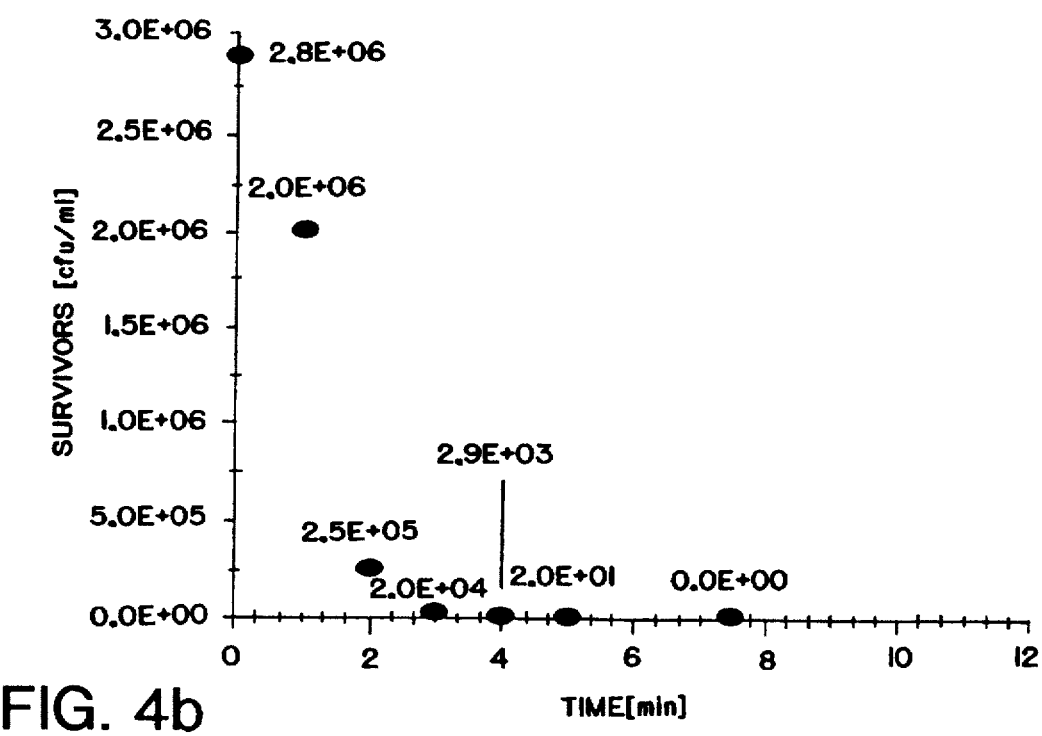
Figure 4C:
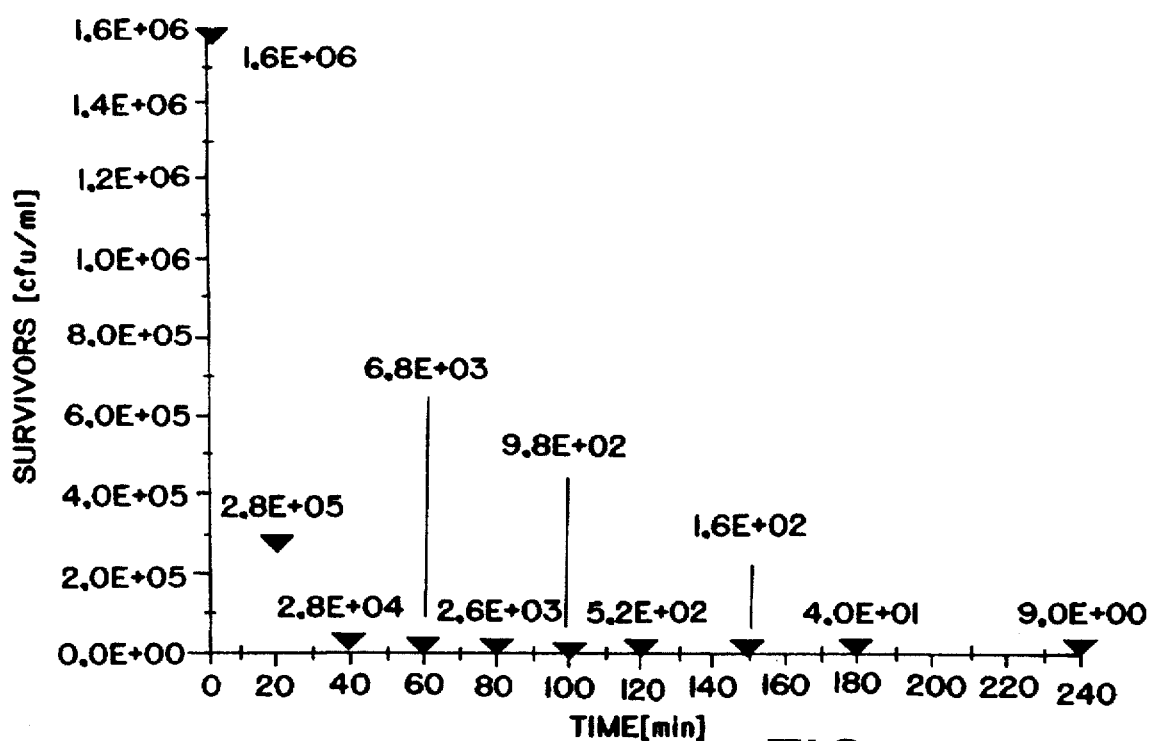
Figure 4D:
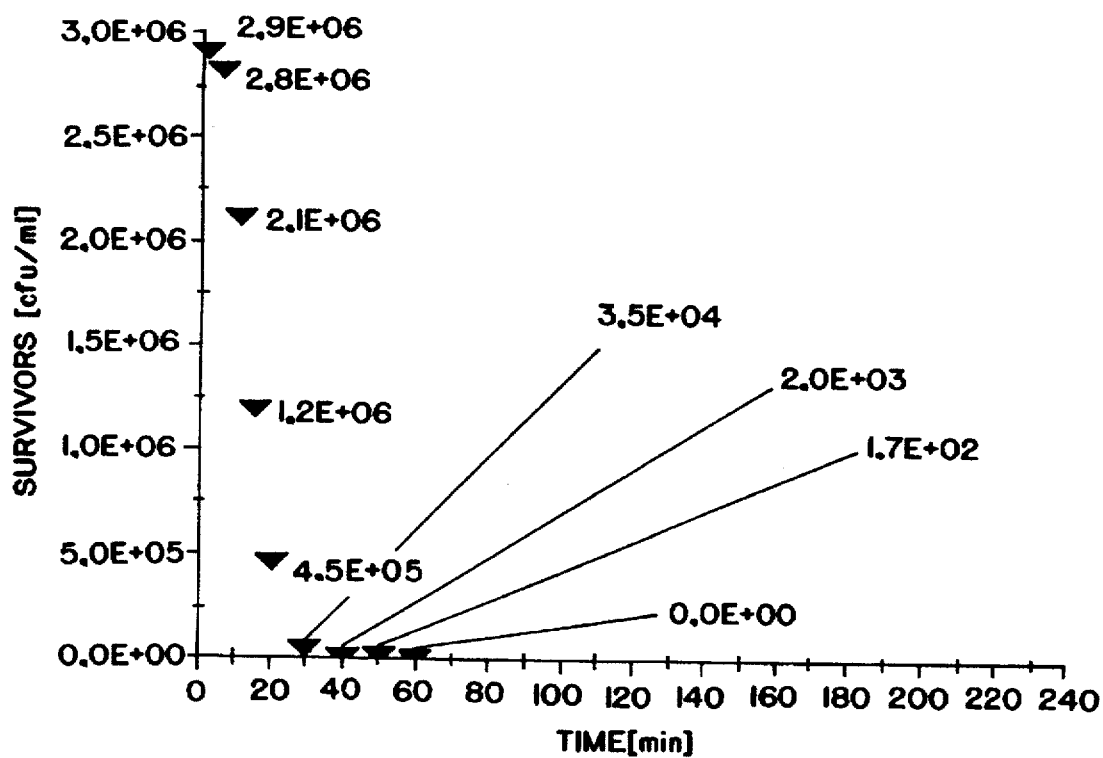

Comparison of $D_{10}$-values of Various Microbicidal Agents Including a Sterilizing Solution of the Present Invention Referring now to FIGS. 3(a) and 3(b), there are shown the $D_{10}$-values of a variety of microbicidal agents against the spores of B. subtilis (ATCC 6633), the $D_{10}$-values for many of the agents being obtained under varying conditions of concentration, pH and temperature. (A $D_{10}$-value is herein defined as the time necessary to reduce an initial germ concentration by one order of magnitude or, in other words, by 90%.) As can be seen, at opposite ends of the spectrum are the peracetic acid (1500 ppm) solution supplemented with 30% ethanol, pH 5, at 25° C., which showed a $D_{10}$-value of 0.4 minutes, as compared to the 0.5N sodium hydroxide solution at 4° C., which showed a $D_{10}$-value of around 860 minutes.

EXAMPLE IV

Effects of Temperature and Ethanol on the Inactivation Kinetics of Sterilizing Solutions of the Present Invention Referring now to FIGS. 4(a) through 4(d), the effects of temperature and ethanol on the inactivation kinetics of sterilizing solutions of the present invention are shown. As can be seen, for example, by comparing FIGS. 4(a) and 4(b) or by comparing FIGS. 4(c) and 4(d), those sterilizing solutions which contain 20% ethanol possess better microbicidal properties than those which do not contain 20% ethanol. In addition, by comparing FIGS. 4(a) and 4(c) or by comparing FIGS. 4(b) and 4(d), it can clearly be seen that by raising the sterilizing temperature from 4° C. to 25° C., the microbicidal effect of the sterilizing solutions are vastly improved.

EXAMPLE V

Sterilization of Q-HyperD™ and S-HyperD™ Chromatography Resins Using a Sterilization Solution of the Present Invention 1 ml of washed and drained Q-HyperD™ silica oxide/polystyrene composite support functionalized with quaternary amine for ion-exchange chromatography (commercially available from BioSepra, Inc., Marlborough, Mass.) was transferred into a 15 ml tube. 1 ml of washed and drained S-HyperD™ silica oxide/polystyrene composite support functionalized with sulfopropyl for ion-exchange chromatography (also commercially available from BioSepra, Inc., Marlborough, Mass.) was transferred into a second 15 ml tube. A blank was performed by adding 1 ml of distilled water to a third 15 ml tube. 10 ml of acetate buffer (0.5M, pH 5) were added to each tube, and the contents of each tube were mixed. After the resin settled, the supernatant from each tube was decanted. 10 ml of spores of B. subtilis (1.9×10$^6$ germs/ml) were added to each tube, and the contents of each tube were mixed. After the resin settled, the supernatant from each tube was again decanted.

10 ml of peracetic acid (1500 ppm in 0.5M acetate buffer, pH 5)were then added to each tube, and the contents of each tube were mixed. After 30 minutes, 0.1 ml $Na_2S_2O_3 \cdot 5H_2O$ (50% w/v) was added to each tube, and the contents of each tube were mixed. After the resin settled, the supernatant from each tube was decanted and replaced by 10 ml sterile acetate buffer (0.5M, pH 5). The buffer was then removed by decanting and replaced with 10 ml sterile Caso Bouillon. The samples were then incubated for 7 days at 30° C., the samples being checked daily for sterility. A second spiking of the samples with spores of B. subtilis was performed after 7 days to rule out the possibility that any observed growth inhibitory effects were attributable to factors other than the sterilization solution. The samples were then checked the day following the second spiking for sterility. The daily sterility evaluations for each of the samples appear below in the TABLE.

TABLE

| | EVALUATION OF STERILITY: STERILE (YES) OR NOT STERILE (NO) | | | | | | | |
|---|---|---|---|---|---|---|---|---|
| SAM-PLE | 1st day | 2nd day | 3rd day | 4th day | 5th day | 6th day | 7th day | 8th day |
| Q-HyperD | YES | YES | YES | YES | YES | YES | YES | 2nd NO |
| S-HyperD | YES | YES | YES | YES | YES | YES | YES | Spike NO |
| Water | YES | YES | YES | YES | YES | YES | YES | NO |

As can be seen from the TABLE, the sterilization solution successfully prevented growth on the various media for seven days. The results on the 8th day confirm that the growth inhibitory effects are attributable to use of the sterilization solution.

EXAMPLE VI

Sterilization of a Phenyl-HyperD™ Chromatography Resin Using a Sterilization Solution of the Present Invention The procedure recited above in connection with Example V was repeated, with the exception that 1 ml of Phenyl-HyperD™ resin was used instead of 1 ml of Q- and S-HyperD™ resins. Phenyl-HyperD™ was prepared by the following procedure: A primary amino-containing HyperD™ resin was obtained from BioSepra Inc. (Paris, France). 10 g of the resin were dried at 70° C. for 4 hours and swollen in 100 ml 1,2-dichlorethane. The matrix was reacted with a bisepoxyrane made from butanediol and epichlorhydrine in the presence of boron trifluoride ethyl etherate as a catalyst, as described by Ulbrich et al. in Collect. Czech. Chem. Commun., 29:1466 (1964), which is incorporated herein by reference. The activated matrix was then reacted with phenylpropylamine at pH 9 in the presence of borhydride at room temperature for 60 minutes and subsequently washed with 300 ml portions of dichlorethane, acetone and water.

Sterility was again observed after seven days of incubation.

EXAMPLE VII

Sterilization of HyperD™ Chromatography Resin Using a Sterilization Solution of the Present Invention 1 ml of HyperD™ silica oxide/polystyrene composite support with functionalized hydrogel filled pores (commercially available from BioSepra, Inc., Marlborough, Mass.) is challenged with B. subtilis and subsequently sterilized using the same procedure set forth in connection with Example V. After the sterilizing procedure, the sterilizing solution is displaced by an excess (i.e., 30 ml) of sterile 1M $NaCO_3$ solution. After the resin settles, the supernatant is decanted. 2 g of BrCN dissolved in 0.5 ml acetonitrile is then sterile filtered into the tube with the resin. The resulting suspension is gently shaken for 20 minutes at room temperature. After the resin settles, the supernatant is decanted, and the resin is washed by the repeated addition and decanting of 10 ml volumes of sterile acetone. After twice washing the activated resin with sterile water, the settled resin is poured into 10 ml of Caso Bouillon and incubated for 7 days at 30° C. After seven days of incubation, no growth is detected. To demonstrate that neither the activated resin nor the byproducts of the activation procedure is attributable for the inhibition of microbial growth, a control gel in Caso Bouillon is challenged with B. subtilis and similarly incubated. Growth is observed.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for sterilizing a chromatography resin that is highly resistant to oxidation by strongly oxidizing agents without generation of toxic end products, said method comprising the step of washing the chromatography resin with an aqueous solution of a percarboxylic acid, said aqueous solution including an acetate buffer in a concentration of about 0.1 to 2M.

2. The method as claimed in claim 1 wherein said percarboxylic acid is peracetic acid.

3. The method as claimed in claim 2 wherein said acetate buffer has a concentration of about 0.5M.

4. The method as claimed in claim 3 wherein said aqueous solution has a pH of about 5.

5. The method as claimed in claim 4 wherein said peracetic acid has a concentration of about 500 mg/l to about 5000 mg/l.

6. The method as claimed in claim 5 wherein said peracetic acid has a concentration of about 1500 mg/l to about 5000 mg/l.

7. The method as claimed in claim 2 wherein said peracetic acid has a concentration of about 500 mg/l to about 5000 mg/l.

8. The method as claimed in claim 7 wherein said peracetic acid has a concentration of about 1500 mg/l to about 5000 mg/l.

9. The method as claimed in claim 2 wherein said washing step is performed at about 4° C. to about 25° C.

10. The method as claimed in claim 1 wherein said aqueous solution has a pH of about 5.

11. The method as claimed in claim 1 wherein the chromatography resin comprises a passivated porous support comprising (i) a porous mineral oxide matrix having interior and exterior surfaces substantially covered by a thin, protective polymer surface coating having innate hydrophobic groups that render said coating susceptible to undesirable non-specific interaction with one or more biological molecules, and (ii) a polymer network derived from a passivation mixture comprising a main monomer, a passivated monomer different from said main monomer, and a crosslinking agent, said mixture having been allowed to come into intimate contact with said surfaces of said coating such that on polymerization of said mixture said innate groups of said coating become deactivated, resulting in the substantial elimination of said undesirable non-specific interaction.

12. A method for sterilizing a chromatography resin that is highly resistant to oxidation by strongly oxidizing agents without generation of toxic end products, said method comprising the step of washing the chromatography resin with an aqueous solution of a percarboxylic acid, said aqueous solution including an acetate buffer in a concentration of about 0.1 to 2M and an alcohol.

13. The method as claimed in claim 12 wherein said percarboxylic acid is peracetic acid.

14. The method as claimed in claim 13 wherein said alcohol is ethanol.

15. The method as claimed in claim 14 wherein the concentration of ethanol in said aqueous solution is no greater than about 40%.

16. The method as claimed in claim 15 wherein the concentration of ethanol in said aqueous solution is about 20%.

17. The method as claimed in claim 13 wherein said acetate buffer has a concentration of about 0.5M.

18. The method as claimed in claim 17 wherein said aqueous solution has a pH of about 5.

19. The method as claimed in claim 18 wherein said peracetic acid has a concentration of about 500 mg/l to about 5000 mg/l.

20. The method as claimed in claim 19 wherein said peracetic acid has a concentration of about 1500 mg/l to about 5000 mg/l.

21. The method as claimed in claim 20 wherein the alcohol in said aqueous solution is ethanol in a concentration of about 20%.

22. The method as claimed in claim 21 wherein said washing step is performed at about 4° C. to about at 25° C.

23. The method as claimed in claim 13 wherein said peracetic acid has a concentration of about 500 mg/l to about 5000 mg/l.

24. The method as claimed in claim 23 wherein said peracetic acid has a concentration of about 1500 mg/l to about 5000 mg/l.

25. The method as claimed in claim 13 wherein said washing step is performed at about 4° C. to about 25° C.

26. The method as claimed in claim 12 wherein said aqueous solution has a pH of about 5.

27. The method as claimed in claim 12 wherein the chromatography resin comprises a passivated porous support comprising (i) a porous mineral oxide matrix having interior and exterior surfaces substantially covered by a thin, protective polymer surface coating having innate hydrophobic groups that render said coating susceptible to undesirable non-specific interaction with one or more biological molecules, and (ii) a polymer network derived from a passivation mixture comprising a main monomer, a passivated monomer different from said main monomer, and a crosslinking agent, said mixture having been allowed to come into intimate contact with said surfaces of said coating such that on polymerization of said mixture said innate groups of said coating become deactivated, resulting in the substantial elimination of said non-specific interaction.

* * * * *